United States Patent
Tsumoto et al.

(10) Patent No.: US 10,143,860 B2
(45) Date of Patent: Dec. 4, 2018

(54) RADIATION THERAPY APPARATUS

(71) Applicant: HITACHI, LTD., Tokyo (JP)

(72) Inventors: Yoshitaka Tsumoto, Tokyo (JP);
Akihiro Miyamoto, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 143 days.

(21) Appl. No.: 15/111,371

(22) PCT Filed: Jan. 21, 2014

(86) PCT No.: PCT/JP2014/051090
§ 371 (c)(1),
(2) Date: Jul. 13, 2016

(87) PCT Pub. No.: WO2015/111132
PCT Pub. Date: Jul. 30, 2015

(65) Prior Publication Data
US 2016/0332001 A1 Nov. 17, 2016

(51) Int. Cl.
*A61N 5/10* (2006.01)
*A61N 5/01* (2006.01)

(52) U.S. Cl.
CPC .............. *A61N 5/1081* (2013.01); *A61N 5/01* (2013.01)

(58) Field of Classification Search
CPC ...... A61N 5/1081; A61N 5/01; A61B 6/4441; A61B 6/4447; A61B 6/4435; A61B 6/44
See application file for complete search history.

(56) References Cited

U.S. PATENT DOCUMENTS

| | | | | |
|---|---|---|---|---|
| 4,150,297 A | * | 4/1979 | Borggren | A61B 6/4464 378/181 |
| 6,461,039 B1 | * | 10/2002 | Klotz | A61B 6/4441 378/196 |
| 2004/0013239 A1 | | 1/2004 | Gregerson et al. | |
| 2008/0197303 A1 | | 8/2008 | Aoi et al. | |
| 2015/0065870 A1 | | 3/2015 | Ishikawa et al. | |

FOREIGN PATENT DOCUMENTS

| | | |
|---|---|---|
| JP | H09-508550 A | 9/1997 |
| JP | H09-304303 A | 11/1997 |
| JP | 2002-325854 A | 11/2002 |
| JP | 2006-021046 A | 1/2006 |

(Continued)

OTHER PUBLICATIONS

Extended European Search Report received for European patent Application No. 14879326.8. dated Jan. 20, 2017, 5 pages.

(Continued)

*Primary Examiner* — Kaylee Wilson (57) ABSTRACT

A radiation therapy apparatus includes: an annular gantry; an irradiation unit which is provided on the gantry and configured to radiate radiation; a support which supports the gantry; a rotation-driving mechanism which is provided between the gantry and the support and rotates the gantry around a horizontal central axis of the gantry. The rotation-driving mechanism includes: annular rails that are provided on the gantry; and sliding members which are provided on regions of the support that correspond to a lower half of the gantry, slidably guide the rails, and receive at least a load of the gantry in a vertical direction.

3 Claims, 9 Drawing Sheets

(56) References Cited

FOREIGN PATENT DOCUMENTS

| JP | 2008-200091 A | 9/2008 |
|---|---|---|
| JP | 2008-200092 A | 9/2008 |
| JP | 4228019 B2 | 2/2009 |
| JP | 2012-125561 A | 7/2012 |
| WO | 2013128770 A1 | 9/2013 |

OTHER PUBLICATIONS

PCT/ISA/210, "International Search Report for International Application No. PCT/JP2014/051090," dated Feb. 18, 2014.
PCT/ISA/237, "Written Opinion of the International Searching Authority for International Application No. PCT/JP2014/051090," dated Feb. 18, 2014.

* cited by examiner

RADIATION THERAPY APPARATUS

RELATED APPLICATIONS

The present application is National Phase of International Application No. PCT/JP2014/051090 filed Jan. 21, 2014, the disclosure of which is hereby incorporated by reference herein in its entirety.

TECHNICAL FIELD

The present invention relates to a radiation therapy apparatus which irradiates a patient with radiation in multiple directions.

BACKGROUND ART

A method of treating tumors includes radiation therapy which irradiates an affected part with radiation. In the radiation therapy, it is preferable that a radiation dose (a dose) for a patient be reduced as small as possible and an affected part be efficiently irradiated with radiation. For this reason, stereotactic radiotherapy through which an affected part of a patient can be irradiated with radiation in multiple directions has been used.

Figure 8:
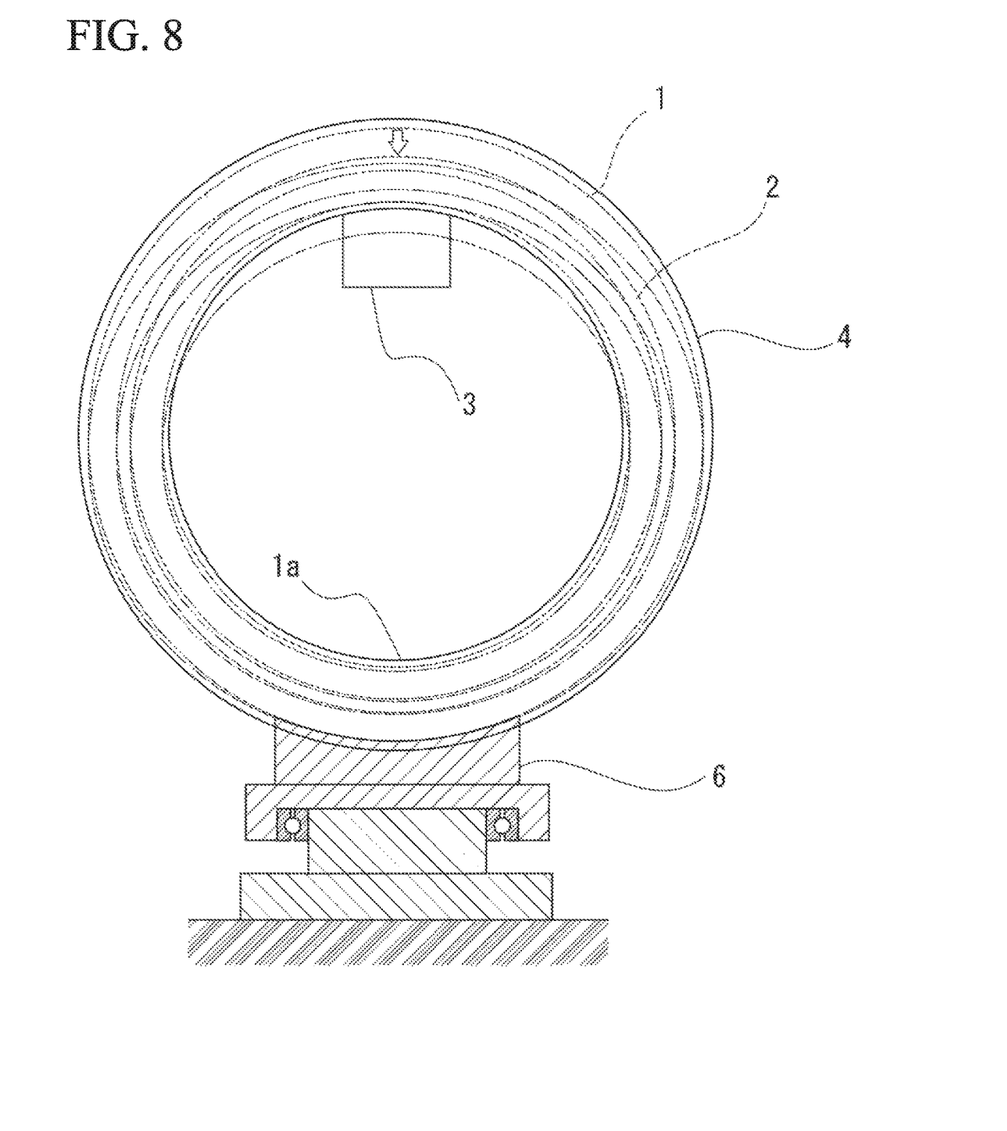
FIG. 8 is a front view showing a driving mechanism of a gantry in a general radiation therapy apparatus.
Figure 9:
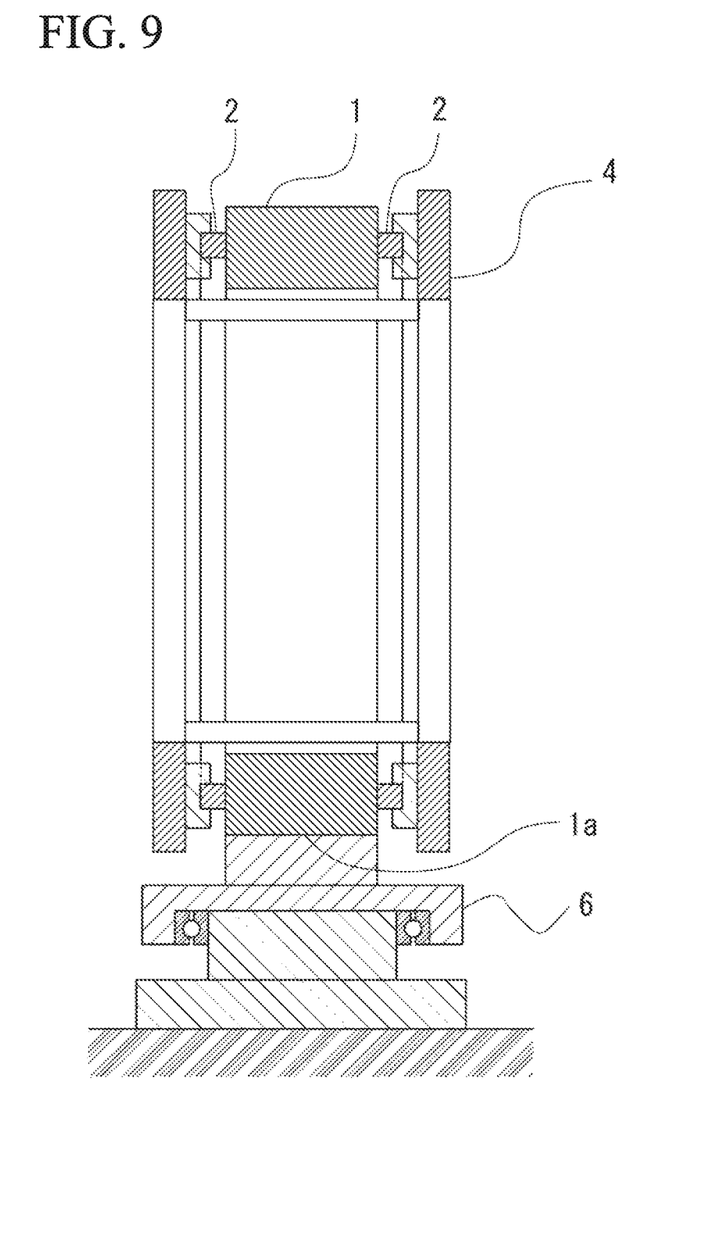
FIG. 9 is a side cross-sectional view showing the driving mechanism of the gantry in the general radiation therapy apparatus.

As shown in FIGS. 8 and 9, a constitution including an annular support frame 1 which is provided to surround a body axis of a patient, annular rails 2 which are provided on lateral surfaces of the support frame 1, and an annular gantry 4 which is pivotable about a horizontal axis along the rails 2 and has a radiation irradiating unit 3 is disclosed in Patent Literature 1 as an apparatus which performs such stereotactic radiotherapy. In such a radiation therapy apparatus, the gantry 4 is pivoted along the rails 2 so that the patient is irradiated with radiation in multiple directions by turning the radiation irradiating unit 3 installed at the gantry 4 about the body axis of the patient.

CITATION LIST

Patent Literature

[Patent Literature 1]
  Japanese Patent No. 4228019

SUMMARY OF INVENTION

Technical Problem

However, in the above-described related art, the annular support frame 1 for supporting the rails 2 should be configured to have a high strength to secure accuracy of the rails 2. As a result, an apparatus weight of the entire radiation therapy apparatus is increased.

Also, with regard to the support frame 1, a lowermost end 1a which is positioned vertically under a central axis of the support frame 1 is supported on a turning mechanism 6 to pivot the support frame 1 about a vertical axis. For this reason, as indicated by a chain double dashed line in FIG. 8, the support frame 1 is easily deformed in an elliptical shape by being crushed in a vertical direction due to a weight of the gantry 4 and a weight of the support frame 1 itself. If the rails 2 are also deformed according to such deformation, positional accuracy of the gantry 4 is adversely affected, and thus correction is required, or it may become difficult for the gantry 4 to turn itself in some cases. A weight thereof is further increased if a strength of the support frame 1 is increased to prevent this.

Also, an increased height of the entire radiation therapy apparatus leads to an increase in size of the apparatus if the turning mechanism 6 is provided about the vertical axis under the lowermost end 1a of the support frame 1.

An aspect of the present invention is for the purpose of providing a radiation therapy apparatus capable of improving positional accuracy of a gantry, suppressing an increase in size of the apparatus, and reducing a weight of the apparatus.

Solution to Problem

In order to accomplish the above-described objects, the present invention adopts the following aspects.

According to a first aspect related to the present invention, a radiation therapy apparatus includes: an annular gantry; an irradiation unit which is provided on the gantry and configured to radiate radiation; a support which supports the gantry; a rotation-driving mechanism which is provided between the gantry and the support and rotates the gantry around a central axis of the gantry, wherein the rotation-driving mechanism comprises: annular rails that are provided on the gantry; and first sliding members which are provided on regions of the support that correspond to a lower half of the gantry, slidably guide the rails, and receive at least a load in a vertical direction of the gantry.

According to a second aspect related to the present invention, in the radiation therapy apparatus, the rotation-driving mechanism in the radiation therapy apparatus of the first aspect may further comprise second sliding members which are provided at positions of the support which are laterally offset with respect to a vertical lower position of the central axis of the gantry, slidably guide the rails, and restrict displacement of the gantry in a horizontal direction.

According to a third aspect related to the present invention, in the radiation therapy apparatus, the first sliding members and the second sliding members in the radiation therapy apparatus of the first or second aspect may be symmetrically disposed in line with respect to a vertical axis passing through the central axis of the gantry.

According to a fourth aspect related to the present invention, the radiation therapy apparatus may further include: a turning mechanism which supports the support in the radiation therapy apparatus of any one of the first to third aspects to be turnable about a vertical axis.

According to a fifth aspect related to the present invention, in the radiation therapy apparatus, the turning mechanism in the radiation therapy apparatus of the fourth aspect may have a rotational shaft with a center in a vertical axis direction, and the first sliding members and the second sliding members may be disposed vertically above the rotational shaft.

According to a sixth aspect related to the present invention, in the radiation therapy apparatus, the turning mechanism in the radiation therapy apparatus of any one of the first to fifth aspects includes a base installed on a floor; turning rails which are provided on one of the base and the support and continue in a circumferential direction centering on the vertical axis; turning guides which are provided on the other of the base and the support and are slidable along the turning rails, wherein an accommodating portion in which at least a portion of the gantry is accommodated in an inner circumferential side of the turning rails may be formed in the base.

Advantageous Effects of Invention

According to a radiation therapy apparatus related to the present invention, it is possible to improve positional accuracy of a gantry, suppress an increase in size of the apparatus, and reduce a weight of the apparatus.

DESCRIPTION OF EMBODIMENTS

Hereinafter, a radiation therapy apparatus related to an embodiment of the present invention will be described on the basis of the drawings.

First Embodiment

Figure 1:
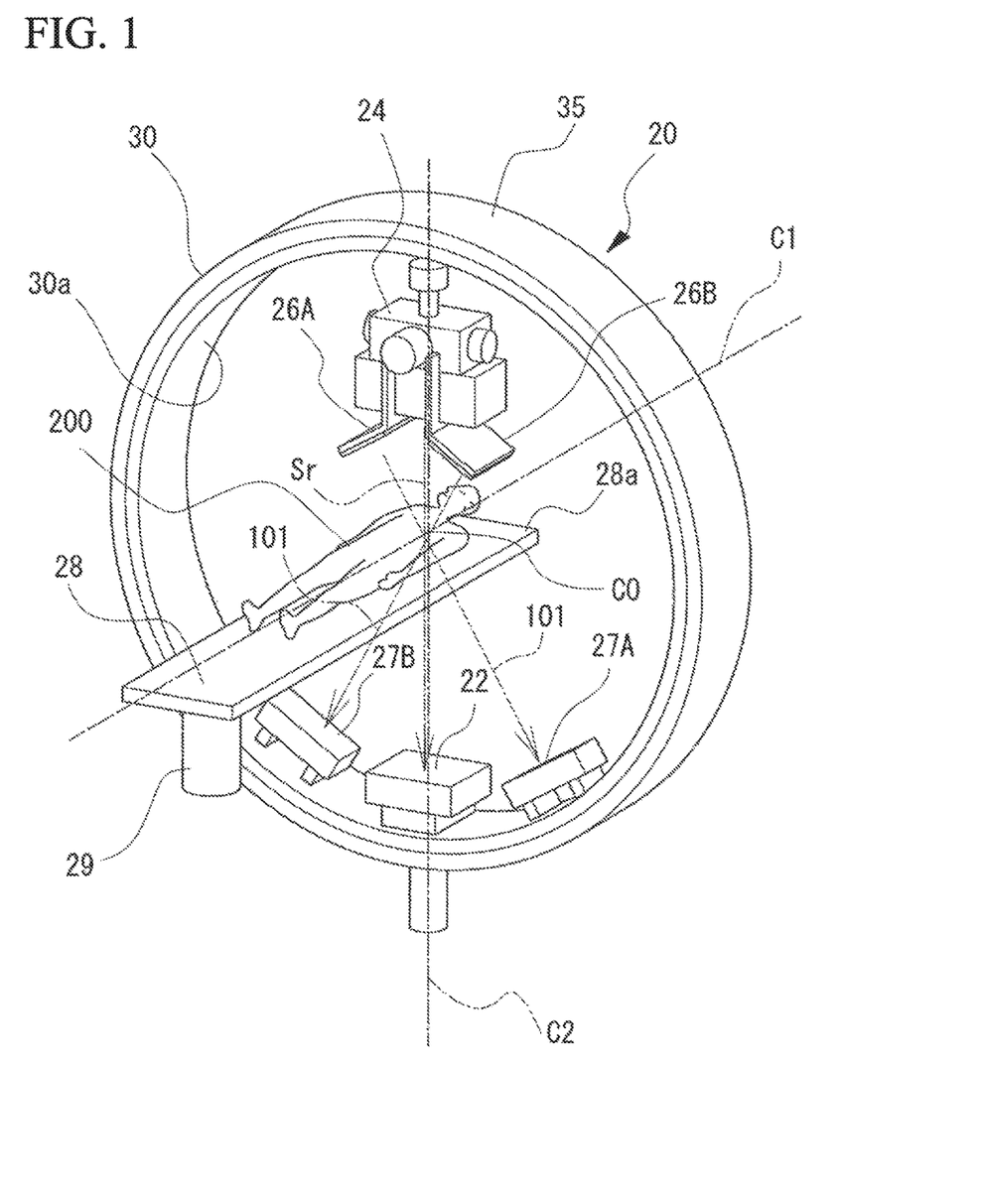
FIG. 1 is a perspective view showing a schematic constitution of a radiation therapy apparatus related to an embodiment of the present invention.

FIG. 1 is a perspective view showing a schematic constitution of a radiation therapy apparatus 20.

As shown in FIG. 1, the radiation therapy apparatus 20 includes a gantry 30 and a radiation irradiating unit (an irradiation unit) 24.

The gantry 30 has a circular cross-sectional cylindrical shape. The gantry 30 is configured to be pivotable in a vertical plane about a horizontal central axis C1 which extends in a horizontal direction using a vertical pivot mechanism (a rotation-driving mechanism) 40A (refer to FIGS. 2 and 3) which will be described below. Also, the gantry 30 is configured to be turnable in a horizontal plane about a vertical central axis (a vertical axis) C2 which extends in a vertical direction using a horizontal turn driving mechanism (a turning mechanism) 50A (refer to FIGS. 2 and 3) which will be described below.

The radiation irradiating unit 24 is supported by an inner circumferential surface 30a of the gantry 30. The radiation irradiating unit 24 is controlled by a control apparatus (not shown) and radiates therapeutic radiation Sr. The therapeutic radiation Sr radiated from the radiation irradiating unit 24 is adjusted to pass through an isocenter C0 set at an intersection of the horizontal central axis C1 and the vertical central axis C2.

As described above, the radiation irradiating unit 24 is supported by the gantry 30 so that the therapeutic radiation Sr is always radiated to pass through the isocenter C0 regardless of a rotational motion about the vertical central axis C2 of the gantry 30 and a rotational motion about the horizontal central axis C1 of the gantry 30.

The radiation therapy apparatus 20 further includes a sensor array 22. The sensor array 22 receives the therapeutic radiation Sr radiated by the radiation irradiating unit 24 and passing through a subject near the isocenter C0 and generates a transmitted image of the subject. For example, a flat panel detector (FPD), an x-ray image intensifier (II), etc. can be used as the sensor array 22.

The radiation therapy apparatus 20 includes diagnostic x-ray sources 26A and 26B and sensor arrays 27A and 27B.

The diagnostic x-ray sources 26A and 26B are disposed at an inner circumferential side of the gantry 30. The diagnostic x-ray sources 26A and 26B are disposed at both sides in a circumferential direction of the gantry 30 to surround a center (in other words, the vertical central axis C2) of the radiation therapy apparatus 20. The diagnostic x-ray sources 26A and 26B are controlled by the control apparatus (not shown) and radiate a diagnostic x-ray 101 toward the isocenter C0. The diagnostic x-ray 101 is a conical cone beam which spreads from one point of the diagnostic x-ray sources 26A and 26B in a conical shape. Here, the diagnostic x-ray 101 is not limited to a conical shape and may be formed as, for example, a pyramidal shape, or the like by cutting out a necessary range using a collimator (not shown).

The sensor arrays 27A and 27B are supported by the inner circumferential surface 30a of the gantry 30. The sensor arrays 27A and 27B are disposed to face the diagnostic x-ray sources 26A and 26B and to surround the isocenter C0. The sensor arrays 27A and 27B receive the diagnostic x-ray 101 radiated from the diagnostic x-ray sources 26A and 26B and passing through a subject near the isocenter C0 and generate a transmitted image of the subject. For example, an FPD, an x-ray II, or the like can be used as the sensor arrays 27A and 27B.

The radiation therapy apparatus 20 further includes a couch 28 and a couch driving apparatus 29. The couch 28 includes an upper surface 28a on which a patient 200 to be treated by the radiation therapy apparatus 20 lies down.

The couch driving apparatus 29 supports the couch 28 at a base (not shown) and moves the couch 28 in response to control of the control apparatus (not shown).

Next, a driving mechanism of the gantry 30 in the radiation therapy apparatus 20 will be described.

Figure 2:
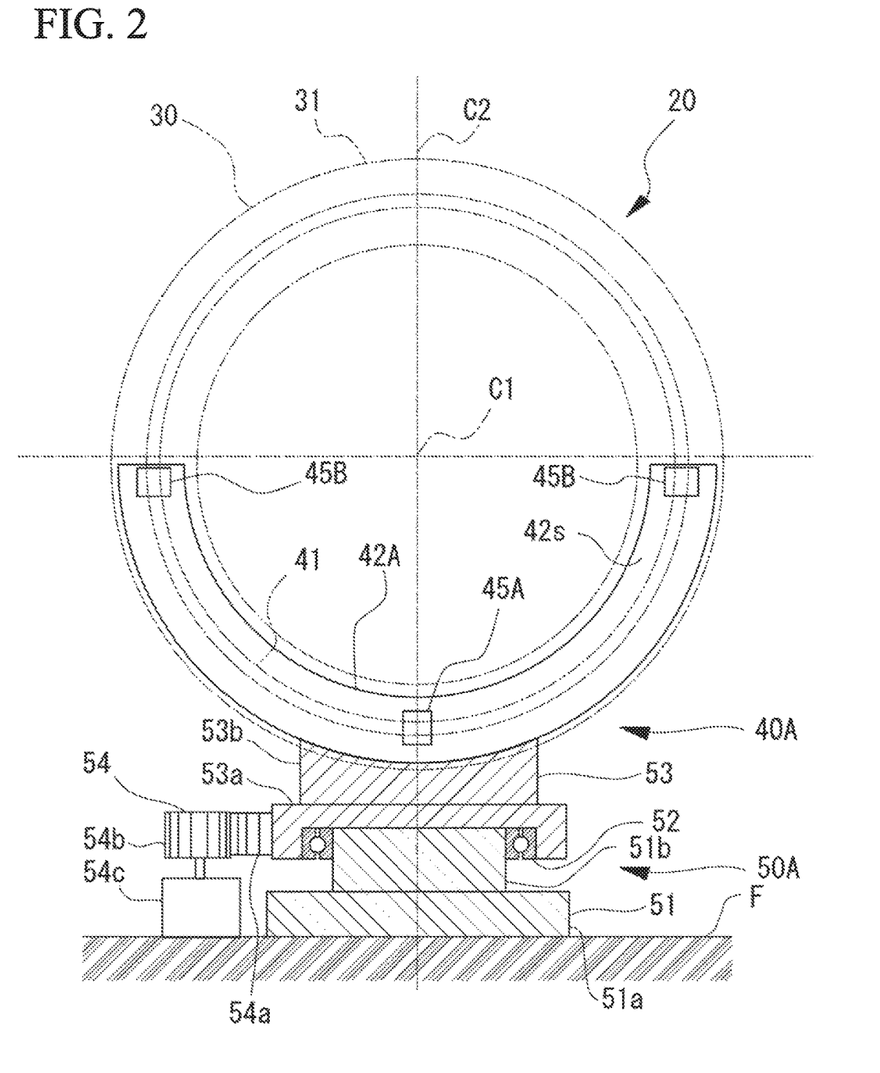
FIG. 2 is a front view showing a driving mechanism of a gantry in a radiation therapy apparatus in a first embodiment.
Figure 3:
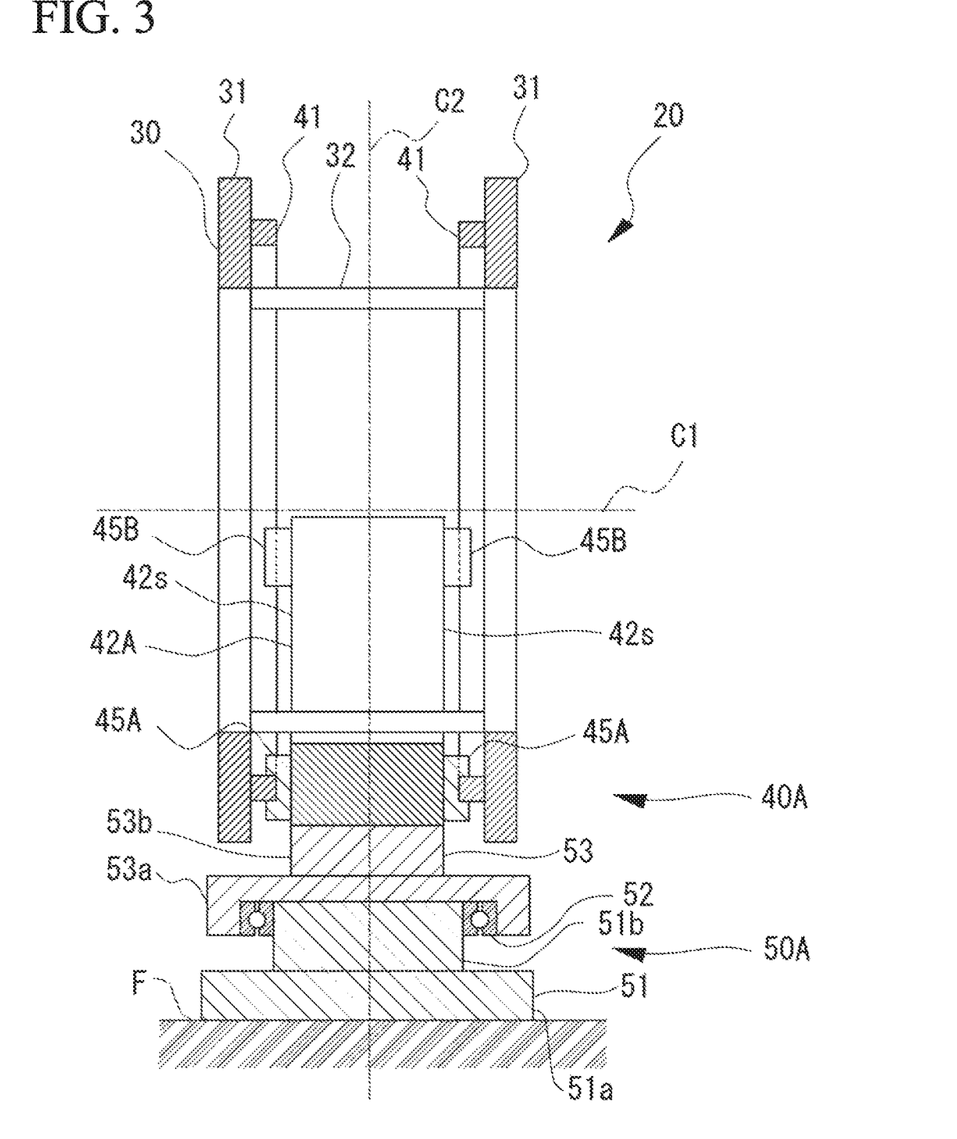
FIG. 3 is a side cross-sectional view showing the driving mechanism of the gantry in the first embodiment.

FIG. 2 is a front view showing a driving mechanism of the gantry 30 in the radiation therapy apparatus 20 in a first embodiment. FIG. 3 is a side cross-sectional view showing the driving mechanism of the gantry 30.

As shown in FIGS. 2 and 3, the radiation therapy apparatus 20 includes a vertical pivot mechanism 40A configured to support the gantry 30 to be pivotable about the horizontal central axis C1 which extends in the horizontal direction and a horizontal turn driving mechanism 50A configured to support the gantry 30 and the vertical pivot mechanism 40A to be turnable about the vertical central axis C2 which extends in the vertical direction.

The gantry 30 includes a pair of annular ring frames 31 and 31 which are arranged in parallel to each other at an interval in a direction along the horizontal central axis C1. The ring frames 31 and 31 are integrally coupled using a plurality of coupling beam materials 32 which are provided at an interval in a circumferential direction. An inner circumferential side of the ring frames 31 is provided with a reinforcing material (not shown) having a truss structure, or the like for reinforcement.

In the ring frames 31, annular gantry rails (rails) 41 are integrally provided at sides at which the ring frames 31 face each other.

As shown in FIG. 1, the gantry 30 is covered by a cover 35, and the radiation therapy apparatus 20, the sensor array 22, the diagnostic x-ray sources 26A and 26B, the sensor arrays 27A and 27B are attached to the inner circumferential surface 30a of the gantry 30 as described above.

As shown in FIGS. 2 and 3, the vertical pivot mechanism 40A includes the gantry rails 41 and sliding members (first sliding members) 45A and sliding members (second sliding members) 45B which are configured to slidably guide the gantry rails 41.

As shown in FIG. 3, the sliding members 45A and 45B are attached to a support 42A disposed between the pair of ring frames 31 and 31 which constitute the gantry 30. The sliding members 45A and 45B are provided at lateral surfaces 42s and 42s of the support 42A which face the pair of ring frames 31 and 31. The support 42A has a semi-annular arc shape which is provided in a range at a lower side than the horizontal central axis C1 of the gantry 30.

As shown in FIGS. 2 and 3, the sliding members 45A are disposed in ranges of the lateral surfaces 42s of the support 42A which are at the lower side than the horizontal central axis C1 of the gantry 30. To be more specific, the sliding members 45A are disposed at a lowermost portion in a circumferential direction of the support 42A. In other words, the sliding members 45A are vertically under the horizontal central axis C1. The sliding members 45A support a lowermost portion in a circumferential direction of the gantry rails 41. A lowermost portion of the gantry rails 41 supported by the sliding members 45A extends substantially in a horizontal direction. Thus, the sliding members 45A restrict vertical displacement of the gantry rails 41 and support the gantry rails 41 to be slidable in the circumferential direction. In other words, the sliding members 45A receive a load in the vertical direction of the gantry 30 via the gantry rails 41.

The sliding members 45B are attached to positions of the lateral surfaces 42s of the support 42A which are laterally offset with respect to a vertical lower position of the horizontal central axis C1 of the gantry 30. The sliding members 45B in the embodiment are arranged at slightly lower positions of both ends of the support 42A than the horizontal central axis C1.

Portions of the gantry rails 41 supported by the sliding members 45B extend substantially in the vertical direction. Thus, the sliding members 45B restrict displacement of the gantry rails 41 in a horizontal direction and support the gantry rails 41 to be slidable in the circumferential direction. In other words, the sliding members 45B restrict displacement of the gantry 30 in a horizontal direction via the gantry rails 41.

The sliding members 45A and the sliding members 45B are symmetrically disposed in line with respect to the vertical central axis C2 passing through the horizontal central axis C1 of the gantry 30.

The gantry 30 is supported by the support 42A to be pivotable about the horizontal central axis C1 via the above-described vertical pivot mechanism 40A. The gantry 30 can be rotatably driven about the horizontal central axis C1 with respect to the support 42A using a driving source (not shown) such as an electric motor.

The horizontal turn driving mechanism 50A includes a lower base member 51, an upper base member 53, and a driving unit 54.

The lower base member 51 is installed on a floor F. The lower base member 51 includes a base plate 51a installed on the floor F and a columnar support shaft portion 51b standing on the base plate 51a. An upper end of the support shaft portion 51b is provided with an annular bearing 52.

The upper base member 53 is installed on the lower base member 51. The upper base member 53 is configured to be rotatable about the vertical central axis C2 via the bearing 52 with respect to the lower base member 51. The upper base member 53 includes a base plate 53a which is supported to be rotatable by the bearing 52 and a rotational shaft portion (a rotational shaft) 53b standing on the base plate 53a. The rotational shaft portion 53b is integrally provided at a lowermost end of the support 42A.

The driving unit 54 rotatably drives the upper base member 53 about the vertical central axis C2. The driving unit 54 includes a gear 54a provided at a side of the upper base member 53, and a motor 54c having a driving gear 54b meshed with the gear 54a.

According to the above-described horizontal turn driving mechanism 50A, when the motor 54c rotates the gear 54a via the driving gear 54b, the support 42A and the gantry 30 are rotatably driven about the vertical central axis C2 together with the upper base member 53. Also, according to the horizontal turn driving mechanism 50A, a load in the vertical direction of the gantry 30 supported by the sliding members 45A, and a load of the support 42A are transferred to the floor F via the support shaft portion 51b and the rotational shaft portion 53b.

The radiation therapy apparatus 20 with the above-described constitution performs treatment as will be described below.

A user first fixes the patient 200 to the couch 28 of the radiation therapy apparatus 20.

The vertical pivot mechanism 40A and the horizontal turn driving mechanism 50A are operated by the control apparatus (not shown) so that the gantry 30 is turned about the horizontal central axis C1 and the vertical central axis C2. Thus, the radiation irradiating unit 24 is moved such that a position of an affected part of the patient 200 is irradiated with the therapeutic radiation Sr at a preset irradiation angle.

Also, the affected part of the patient 200 is irradiated with a preset dose of therapeutic radiation Sr using the radiation irradiating unit 24.

Therefore, according to the radiation therapy apparatus 20 in the above-described first embodiment, the gantry rails 41 are configured to be provided at a side of the annular gantry 30, and the sliding members 45A which guide the gantry rails 41 are configured to be provided at the support 42A. Thus, the sliding members 45A and 45B and support 42A can be provided in regions corresponding to a lower half which is in a range at a lower side than the horizontal central axis C1 of the gantry 30. For this reason, there is no need to set the support 42A to be an annular shape. As a result, vertical deformation of the support 42A due to its own weight is suppressed, and the support 42A can be reduced in size and weight.

The sliding members 45A support the load in the vertical direction of the gantry 30, and the sliding members 45B restrict displacement of the gantry 30 in a horizontal direction. Thus, the gantry 30 can be stably rotated.

Also, the sliding members 45A and the sliding members 45B are symmetrically disposed in line with respect to the vertical central axis C2 of the gantry 30 so that they can stably support the gantry 30 to be pivotable.

The radiation therapy apparatus 20 includes the horizontal turn driving mechanism 50A which supports the support 42A to be turnable about the vertical central axis C2 so that the gantry 30 can be turned about the vertical axis. As a result, a degree of freedom of an irradiation direction of the therapeutic radiation Sr with respect to the patient 200 in the radiation irradiating unit 24 can be increased.

With such a constitution, the sliding members 45A which receive the load in the vertical direction of the gantry 30 are disposed vertically above the support shaft portion 51b and the rotational shaft portion 53b so that the load in the vertical direction of the gantry 30 supported by the sliding members 45A is efficiently transferred to the floor F via the support shaft portion 51b and the rotational shaft portion 53b.

Second Embodiment

Next, a second embodiment of the radiation therapy apparatus related to the present invention will be described. In the second embodiment described below, since the second embodiment is different from the first embodiment only in view of the constitution of a vertical pivot mechanism 40B, the same components as those of the first embodiment will be described with the same reference numerals, and overlapping description with the first embodiment will be omitted.

Figure 4:
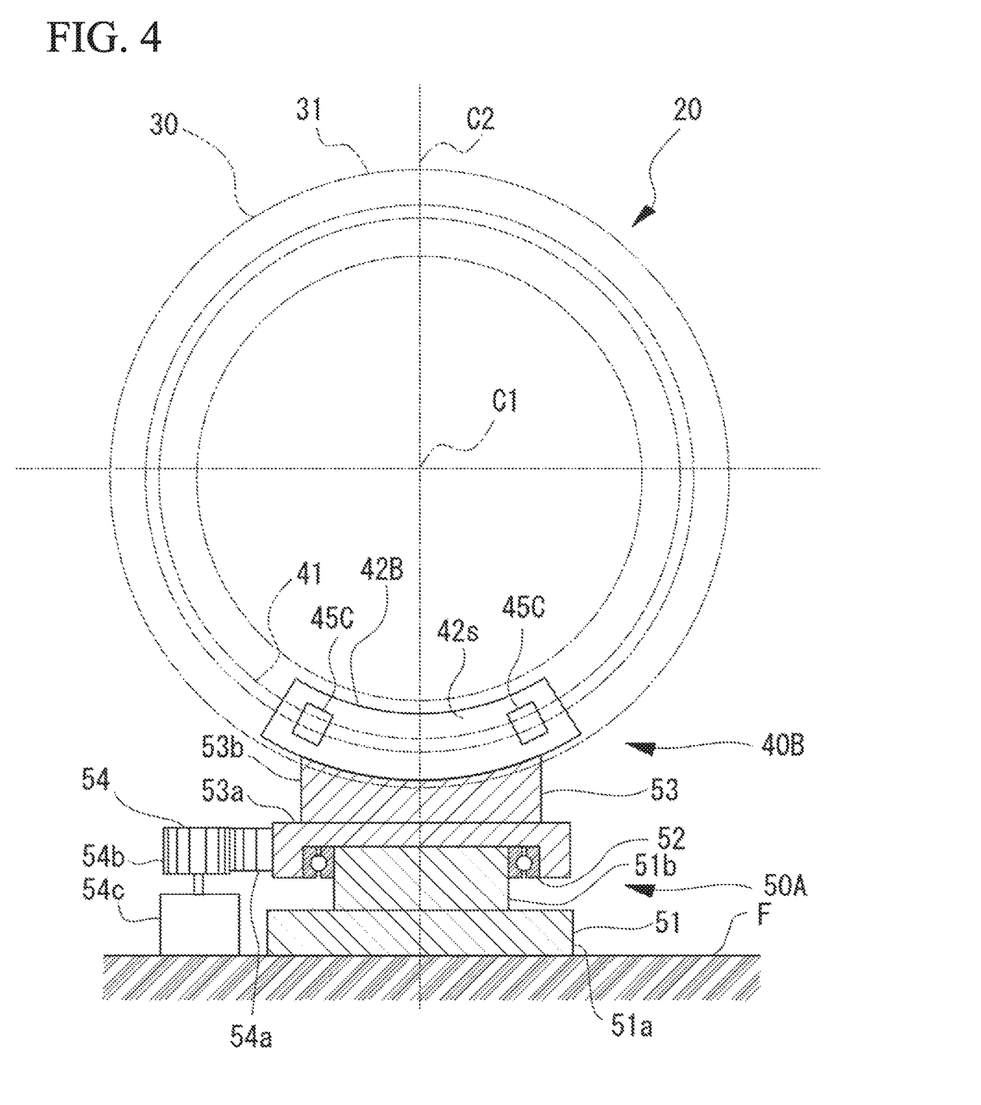
FIG. 4 is a front view showing a driving mechanism of a gantry in a radiation therapy apparatus in a second embodiment.
Figure 5:
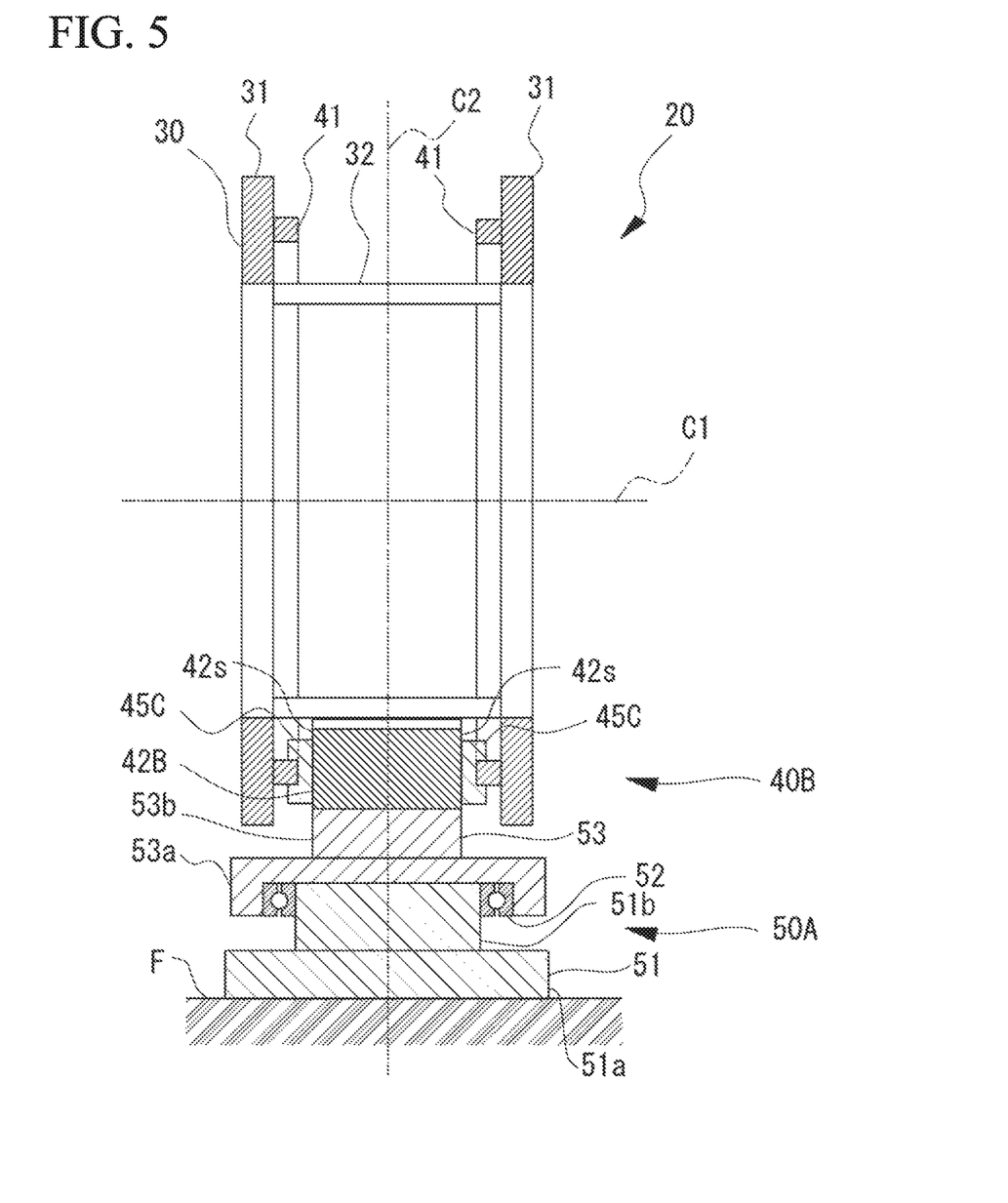
FIG. 5 is a side cross-sectional view showing the driving mechanism of the gantry in the second embodiment.

FIG. 4 is a front view showing a driving mechanism of the gantry 30 in the radiation therapy apparatus 20 in the second embodiment. FIG. 5 is a side cross-sectional view showing the driving mechanism of the gantry 30.

As shown in FIGS. 4 and 5, the vertical pivot mechanism 40B in the embodiment includes the gantry rails 41, sliding members (a first sliding member and a second sliding member) 45C and 45C which slidably guide the gantry rails 41.

The sliding members 45C and 45C are provided at the lateral surfaces 42s and 42s of a support 42B. The support 42B has a circular arc shape which is provided in a range at a lower side than the horizontal central axis C1 of the gantry 30.

The sliding members 45C and 45C are disposed at positions which are under the horizontal central axis C1 of the gantry 30 and are laterally offset with respect to a vertically lower side of the horizontal central axis C1 of the gantry 30. Also, the sliding members 45C and 45C are symmetrically disposed in line with respect to the vertical central axis C2 of the gantry 30.

The sliding members 45C and 45C are disposed in a range which is vertically above the rotational shaft portion 53b of the horizontal turn driving mechanism 50A. In addition, the sliding members 45C and 45C are provided vertically above the bearing 52 of the horizontal turn driving mechanism 50A.

With such a constitution, the gantry rails 41 obliquely extend at portions of the sliding members 45C and 45C. For this reason, the sliding members 45C and 45C have a function of receiving a load in the vertical direction of the gantry 30 and a function of restricting a displacement of the gantry 30 in a horizontal direction. In other words, the sliding members 45C and 45C have the functions of the first sliding member and the second sliding member of the present invention together.

Therefore, according to the above-described second embodiment, as in the first embodiment, the gantry rails 41 are configured to be provided at the side of the annular gantry 30, and the sliding members 45C and 45C which guide the gantry rails 41 are configured to be provided at the support 42B so that there is no need to set the support 42B to be an annular shape as in the related art. As a result, the support 42B can be reduced in size and weight.

The sliding members 45C and 45C support the load in the vertical direction of the gantry 30 and restrict a displacement of the gantry 30 in a horizontal direction so that the gantry 30 can be stably rotated.

The sliding members 45C and 45C are disposed vertically above the bearing 52 of the horizontal turn driving mechanism 50A in the range which is vertically above the rotational shaft portion 53b of the horizontal turn driving mechanism 50A so that the load in the vertical direction of the gantry 30 supported by the sliding members 45C and 45C can be efficiently transferred to the floor F via the rotational shaft portion 53b.

The sliding members 45C and 45C are disposed vertically above the rotational shaft portion 53b of the horizontal turn driving mechanism 50A so that a length in the circumferential direction and a height of the support 42B can be suppressed when compared with the support 42A in the above-described first embodiment. As a result, the support 42B can be further reduced in size and weight.

Third Embodiment

Next, a third embodiment of the radiation therapy apparatus related to the present invention will be described. In the third embodiment described below, since the third embodiment is mainly different from the first embodiment only in view of the constitution of the horizontal turn driving mechanism, the same components as those of the first embodiment will be described with the same reference numerals, and overlapping description with the first embodiment will be omitted.

Figure 6:
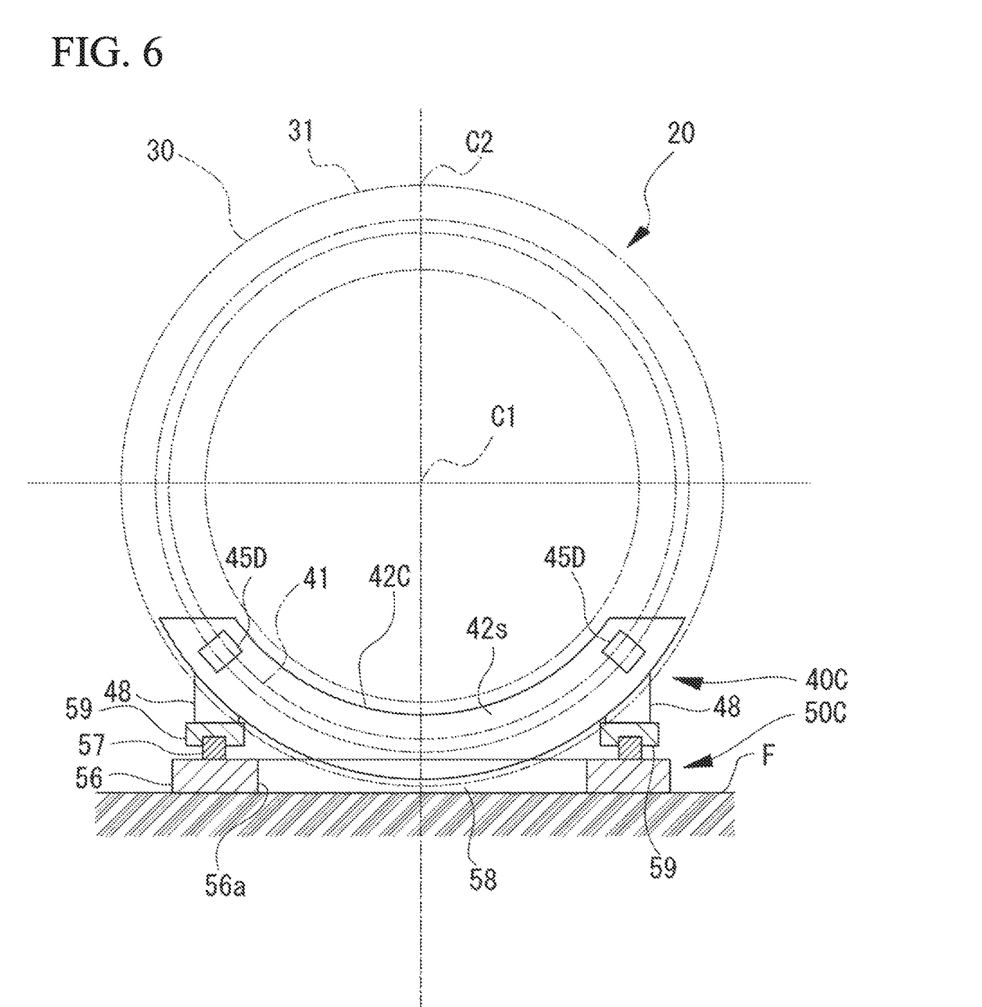
FIG. 6 is a front view showing a driving mechanism of a gantry in a radiation therapy apparatus in a third embodiment.
Figure 7:
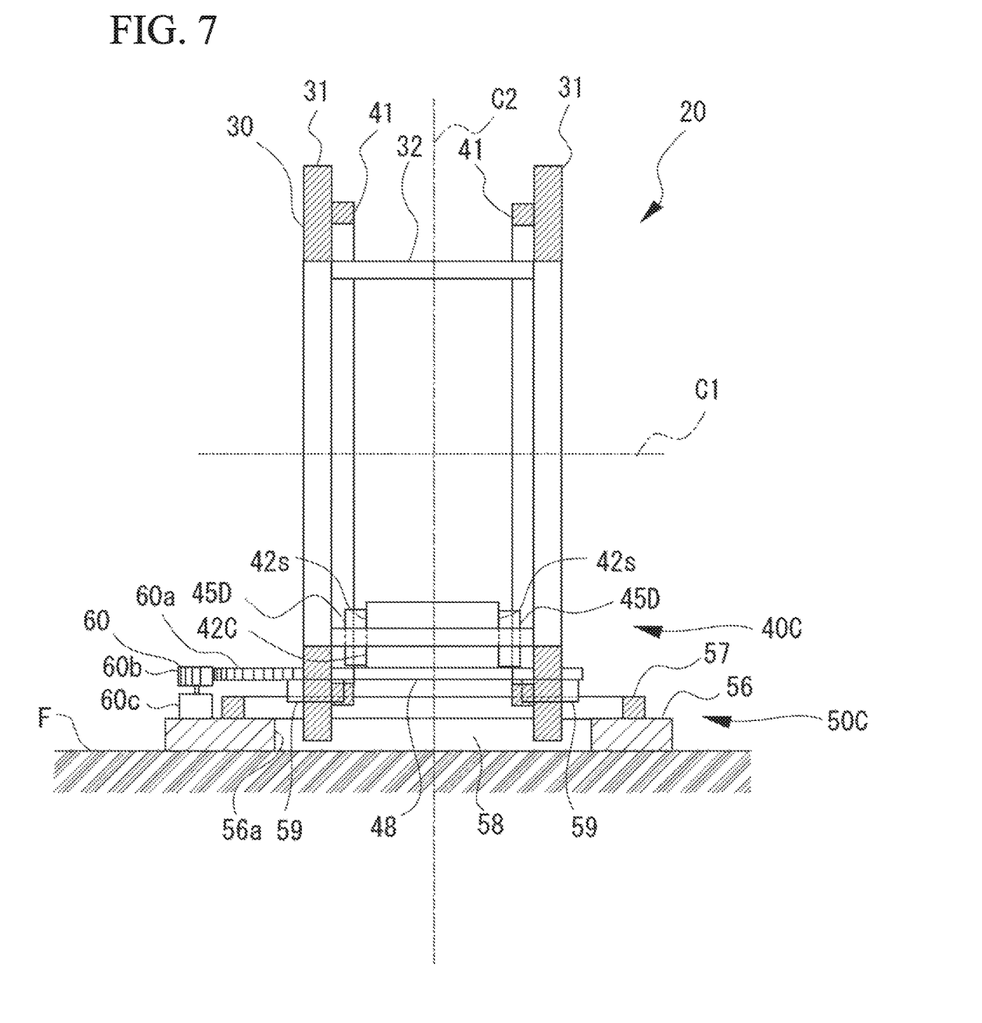
FIG. 7 is a side cross-sectional view showing the driving mechanism of the gantry in the third embodiment.

FIG. 6 is a front view showing a driving mechanism of the gantry 30 in the radiation therapy apparatus 20 in the third embodiment. FIG. 7 is a side cross-sectional view showing the driving mechanism of the gantry 30.

As shown in FIGS. 6 and 7, the radiation therapy apparatus 20 in the embodiment includes a vertical pivot mechanism 40C which supports the gantry 30 to be pivotable about the horizontal central axis C1 extending in the horizontal direction and a horizontal turn driving mechanism (a turning mechanism) 50C which supports the gantry 30 and the vertical pivot mechanism 40C to be turnable about the vertical central axis C2 extending in the vertical direction.

The vertical pivot mechanism 40C includes the gantry rails 41 and sliding members (a first sliding member and a second sliding member) 45D and 45D which slidably guide the gantry rails 41.

The sliding members 45D and 45D are provided at both ends in a circumferential direction of a support 42C on the lateral surfaces 42s and 42s of the support 42C. The support 42C has a circular arc shape which is provided in a range at a lower side than the horizontal central axis C1 of the gantry 30.

Supporting legs 48 which extend in the vertical downward direction are integrally formed at both ends in the circumferential direction of the support 42C.

The gantry rails 41 obliquely extend at portions supported by the sliding members 45D and 45D. In other words, the sliding members 45D and 45D have a function of receiving a load in the vertical direction of the gantry 30 and a function for restricting a displacement of the gantry 30 in a horizontal direction as in the sliding members 45C and 45C in the second embodiment. In other words, the sliding members 45D and 45D have the functions of the first sliding member and the second sliding member of the present invention together.

The horizontal turn driving mechanism 50C includes a base 56 installed on the floor F, turning rails 57, turning guides 59, and a driving source 60.

The turning rails 57 are provided on the base 56 and are provided in an annular shape which continues in the circumferential direction centering on the vertical central axis C2. An opening portion 56a is formed at an inner circumferential side of the turning rails 57 in the base 56.

An accommodating portion 58 is formed by the base 56 and the floor F at the inner circumferential side of the turning rails 57 in the base 56. At least a portion of lower end of the gantry 30 and the support 42C is accommodated in the accommodating portion 58.

Here, for example, a concave portion is formed in the floor F so that the deeper accommodating portion 58 can be formed. In this case, the gantry 30 and the support 42C can be further accommodated in the accommodating portion 58.

The turning guides 59 are configured to be slidable along the turning rails 57. The turning guides 59 are provided at lower ends of the support legs 48 of the support 42C. The at least two turning guides 59 are provided on a lower surface of the support 42C at an interval in a circumferential direction of the turning rails 57. Thus, the support 42C is supported to be turnable about the vertical central axis C2.

Here, the sliding members 45D are disposed in ranges which are vertically above the turning guides 59 and the support legs 48.

For example, the driving source 60 is integrally formed with the support 42C. The driving source 60 includes a circular arc-shaped gear 60a which is concentrically formed with one of the turning rails 57, and a motor 60c having a driving gear 60b meshed with the gear 60a. The driving gear 60b is rotatably driven by the motor 60c so that the support 42C and the gantry 30 can be turned about the vertical central axis C2 along with the circular arc-shaped gear 60a.

Therefore, according to the above-described third embodiment, the accommodating portion 58 is formed at the inner circumferential side of the base 56 and the turning rails 57 so that at least a lowermost portion of the gantry 30 and the support 42C can be accommodated Thus, a height of the radiation therapy apparatus 20 can be suppressed.

Since the motor 60c which constitutes the driving source 60 can be integrally formed with the base 56, an installation process can be easily performed without separately performing a foundation task of preparing an installation surface to install the motor 60c.

The sliding members 45D and 45D are disposed vertically above the turning guides 59 and the support legs 48 so that the load in the vertical direction of the gantry 30 supported by the sliding members 45D and 45D can be efficiently transferred to the floor F via the turning guides 59, the support legs 48, the turning rails 57, and the base 56.

The gantry rails 41 are provided at the side of the annular gantry 30, and the sliding members 45D and 45D which guide the gantry rails 41 are provided at the support 42C so that there is no need to set the support 42C to be an annular shape as in the above-described first embodiment. As a result, the support 42C can be reduced in size and weight.

The sliding members 45D and 45D receive the load in the vertical direction of the gantry 30 and restrict a displacement of the gantry 30 in a horizontal direction so that the gantry 30 can be stably rotated.

Also, the sliding members 45D and 45D are symmetrically disposed in line with respect to the vertical central axis C2 passing through the central axis of the gantry 30 so that the gantry can be stably supported to be pivotable.

Another Embodiment

Note that the present invention is not limited to the above-mentioned embodiments and includes various modified examples of the above-described embodiments without departing from the gist of the present invention. In other words, specific shapes and configurations described in the embodiments are merely examples and can be appropriately changed.

For example, in the second and third embodiments, two sliding members 45C and 45C and two sliding members 45D and 45D are configured to be provided. However, the second and third embodiments are not limited to such a constitution. An even number (four or more) of sliding members 45C and 45C and sliding members 45D and 45D may be disposed as long as they are disposed to surround the vertical central axis C2 of the gantry 30. Also, dispositions of the sliding members 45C and 45C and the sliding members 45D and 45D are not limited to disposition which is symmetrically in line with respect to the vertical central axis C2 of the gantry 30 and can also be an asymmetrical disposition.

The sliding members 45A which receive a load in the vertical direction of the gantry 30 may be provided at a position which is a lowermost portion of the support 42B between the two sliding members 45C and 45C and between the two sliding members 45D and 45D which has been described above as in the first embodiment.

In the first and second embodiments, the sliding members 45A and 45C are disposed in the range which is vertically above the support shaft portion 51b and the rotational shaft portion 53b of the horizontal turn driving mechanism 50A. However, the present invention is not limited to this constitution, and for example, the sliding members 45A and 45C can also be disposed out of the range which is vertically above the support shaft portion 51b and the rotational shaft portion 53b of the horizontal turn driving mechanism 50A. In addition, the plurality of sliding members 45A and 45C may be provided in the range which is vertically above the rotational shaft portion 53b. The plurality of sliding members 45A and 45C may be symmetrically disposed to surround a position which is vertically above the rotational shaft portion 53b.

Similarly, in the third embodiment, the sliding members 45D and 45D are configured to be disposed vertically above the turning guides 59 and the support legs 48. However, the present invention is not limited to this constitution. For example, the plurality of sliding members 45D may be provided in the range which is vertically above the turning guides 59 and the support legs 48. The plurality of sliding members 45D may be symmetrically disposed to surround a position which is vertically above the turning guides 59 and the support legs 48.

In the third embodiment, a case in which the base 56 is provided with the turning rails 57, and the support 42C is provided with the turning guides 59 has been described. However, the support 42C may be provided with the turning rails 57 and the base 56 may be provided with the turning guides 59.

Shapes of the supports 42A, 42B, and 42C are not limited to a circular arc shape. The supports 42A, 42B, and 42C can also be another shape such as, for example, a V shape, a concave shape, etc. as long as the sliding members 45A to 45D can be supported at a predetermined position. Column-shaped supports which support the sliding members 45A to 45D may be individually provided. The supports 42A, 42B, and 42C can also have an annular shape for the purpose of providing various apparatuses, or the like.

INDUSTRIAL APPLICABILITY

A gantry is provided with annular rails, and first sliding members which slidably guide the rails and which receive at least a load in a vertical direction of the gantry are provided on a region corresponding to a lower half of the gantry in a support so that positional accuracy of the gantry can be increased, an increase in size of an apparatus can be suppressed, and a weight of the apparatus can be reduced.

REFERENCE SIGNS LIST

20 Radiation therapy apparatus
22 Sensor array
24 Radiation irradiating unit (irradiation unit)
26A, 26B Radiation source
27A, 27B Sensor array
28 Couch
28a Upper surface
29 Couch driving apparatus
30 Gantry
31 Ring frame
32 Coupling beam material
35 Cover
40A, 40B, 40C Vertical pivot mechanism (rotation-driving mechanism)
41 Gantry rail (rail)
42A, 42B, 42C Support
42s Lateral surface
45A Sliding member (first sliding member)
45B Sliding member (second sliding member)
45C Sliding member (first sliding member, second sliding member)
45D Sliding members (first sliding member, second sliding member)
48 Supporting leg
50A, 50C Horizontal turn driving mechanism (turning mechanism)
51 Lower base member
51a Base plate
51b Support shaft portion
52 Bearing
53 Upper base member
53a Base plate
53b Rotational shaft portion (rotational shaft)
54 Driving unit
54a Gear
54b Driving gear
54c Motor
56 Base
56a Opening portion
57 Turning rail
58 Accommodating portion
59 Turning guide
60 Driving source
60a Gear
60b Driving gear
60c Motor
101 Diagnostic x-ray
200 Patient
C0 Isocenter
C0 Horizontal central axis
C2 Vertical central axis (vertical axis)
F Floor
Sr Therapeutic radiation

The invention claimed is:

1. A radiation therapy apparatus comprising:
an annular gantry;
an irradiation unit which is provided on the gantry and configured to radiate radiation;
a support which supports the gantry;
a rotation-driving mechanism which is provided between the gantry and the support and rotates the gantry around a central axis of the gantry, wherein the rotation-driving mechanism comprises:
annular rails that are provided on the gantry;
first sliding members which are provided on regions of the support that correspond to a lower half at a lower side than a horizontal central axis of the gantry to slidably guide the annular rails and receive at least a load in a vertical direction of the gantry; and
a turning mechanism which supports the support to be turnable about a vertical axis, wherein the turning mechanism comprises:
a base installed on a floor;
turning rails which are provided on one of the base and the support and continue in a circumferential direction centering on the vertical axis;
turning guides which are provided on the other of the base and the support and are slidable along the turning rails; and
an accommodating portion formed in the base, in which at least a portion of the gantry is accommodated between inner circumferential sides of the turning rails.

2. The radiation therapy apparatus according to claim 1, wherein the rotation-driving mechanism further comprises second sliding members which are provided at positions of the support which are laterally offset with respect to a vertical lower position of the central axis of the gantry to slidably guide the annular rails and restrict displacement of the gantry in a horizontal direction.

3. The radiation therapy apparatus according to claim 2, wherein the first sliding members and the second sliding members are symmetrically disposed in line with respect to a vertical axis passing through the central axis of the gantry.

* * * * *